United States Patent
Redlich et al.

(10) Patent No.: US 6,875,797 B2
(45) Date of Patent: Apr. 5, 2005

(54) RESIN IMMOBILIZED BIOCIDE

(75) Inventors: George Harvey Redlich, Norristown, PA (US); Roger Gerard Hamel, Newtown, PA (US); Nuno Maurice Rei, Boxford, MA (US)

(73) Assignee: Rohm and Haas Company, Philadelphia, PA (US)

( * ) Notice: Subject to any disclaimer, the term of this patent is extended or adjusted under 35 U.S.C. 154(b) by 85 days.

(21) Appl. No.: 10/085,156

(22) Filed: Feb. 27, 2002

(65) Prior Publication Data

US 2002/0169230 A1 Nov. 14, 2002

Related U.S. Application Data

(60) Provisional application No. 60/273,962, filed on Mar. 7, 2001.

(51) Int. Cl.$^7$ .................................................. C08K 5/34
(52) U.S. Cl. ......................................... 523/122; 524/94
(58) Field of Search ............................. 523/122; 524/94

(56) References Cited

U.S. PATENT DOCUMENTS

| | | |
|---|---|---|
| 4,086,297 A | 4/1978 | Rei et al. |
| 4,243,403 A | 1/1981 | Lewis et al. |
| 4,542,169 A | 9/1985 | Costerton |
| 4,789,692 A | 12/1988 | Rei et al. |
| 4,988,236 A | 1/1991 | Ramsey et al. |
| 5,178,495 A | 1/1993 | Cameron et al. |
| 5,703,105 A | 12/1997 | Redlich et al. |
| 6,528,556 B1 * | 3/2003 | Herbst et al. ............... 523/122 |

FOREIGN PATENT DOCUMENTS

| | | |
|---|---|---|
| EP | 0856552 A1 | 8/1998 |
| WO | WO 9901514 A | 1/1999 |

* cited by examiner

Primary Examiner—Kriellion A. Sanders
(74) Attorney, Agent, or Firm—Thomas D. Rogerson; Kenneth Crimaldi

(57) ABSTRACT

The present invention relates to a composition comprising:
 (a) 85% to 99% by weight of a resin selected from the group consisting of Ethylene-Vinyl Acetate-Carbon Monoxide; Styrene-Butadiene-Styrene; Styrene-Maleic Anhydride; Styrene-Methyl Methacrylate; Thermoplastic polyurethane; Ethylene-Vinyl Acetate and Acrylic Rubber; and mixtures thereof;
 (b) 1% to 15% by weight of a biocide selected from the group consisting of 4,5,-dichloro-2-n-octyl-4-isothiazolone-3-one biocide (DCIOT) and 2-n-octyl-4-isothiazolin-3-one (OIT).

4 Claims, No Drawings

RESIN IMMOBILIZED BIOCIDE

This application claims the benefit of provisional application No. 60/273,962, filed Mar. 7, 2001.

BACKGROUND OF THE INVENTION

The present invention relates to a composition comprising a specific biocide and a resin. Said composition is useful in preparing plastic articles. The plastics articles include, but are not limited to, HDPE, LDPE, other polyolefin resins, EPDM, thermoplastic polyurethanes, styrenics, and thermoplastic elastomers. The presence of the composition, of the present invention, in the plastic article serves to inhibit the growth of bacteria, mold, and fungi.

Resin/biocide compositions are disclosed in U.S. Pat. No. 4,086,297, U.S. Pat. No. 4,789,692, U.S. Pat. No. 4,988,236, and U.S. Pat. No. 5,178,495. However, Applicants have discovered a new resin/biocide composition that is compatible with resins previously considered hard to compatibilize with biocides. Applicants have achieved a new and useful resin/biocide composition not described in the art.

STATEMENT OF THE INVENTION

The present invention relates to a composition comprising:
(a) 85% to 99% by weight of a resin selected from the group consisting of Ethylene-Vinyl Acetate-Carbon Monoxide; Styrene-Butadiene-Styrene; Styrene-Maleic Anhydride; Styrene-Methyl Methacrylate; Thermoplastic polyurethane; Ethylene-Vinyl Acetate and Acrylic Rubber; and mixtures thereof;
(b) 1% to 15% by weight of a biocide selected from the group consisting of 4,5,-dichloro-2-n-octyl-4-isothiazolin-3-one (DCOIT) and 2-n-octyl-4-isothiazolin-3-one (OIT).

DETAILED DESCRIPTION OF THE INVENTION

The present invention relates to a composition comprising:
(a) 85% to 99% by weight of a resin selected from the group consisting of Ethylene-Vinyl Acetate-Carbon Monoxide; Styrene-Butadiene-Styrene; Styrene-Maleic Anhydride; Styrene-Methyl Methacrylate; Thermoplastic polyurethane; Ethylene-Vinyl Acetate and Acrylic Rubber; and mixtures thereof;
(b) 1% to 15% by weight of a biocide selected from the group consisting of 4,5,-dichloro-2-n-octyl-4-isothiazolin-3-one (DCOIT) and 2-n-octyl-4-isothiazolin-3-one (OIT).

Resins useful in the practice of the present invention include, but are not limited to, Ethylene-Vinyl Acetate-Carbon Monoxide; Styrene-Butadiene-Styrene; Styrene-Maleic Anhydride; Styrene-Methyl Methacrylate; Thermoplastic polyurethane; Ethylene-Vinyl Acetate and Acrylic Rubber and mixtures thereof.

The preferred resins are: Ethylene-Vinyl Acetate-Carbon Monoxide; Styrene-Butadiene-Styrene; Styrene-Maleic Anhydride; Styrene-Methyl Methacrylate; Thermoplastic polyurethane; Ethylene-Vinyl Acetate and Acrylic Rubber.

The more preferred resin is: Ethylene-Vinyl Acetate-Carbon Monoxide; Styrene-Butadiene-Styrene; Styrene-Maleic Anhydride; and Styrene-Methyl Methacrylate;

The most preferred resin is: Ethylene-Vinyl Acetate-Carbon Monoxide.

The preferred range of resins in the composition of the present invention is 85 percent to 99 percent (%) by weight, more preferably 88 to 92% by weight; most preferably 90% by weight.

The biocides useful in the practice of the present invention are 4,5-dichloro-2-n-octyl-4-isothiazolin-3-one (DCOIT) and 2-n-octyl-4-isothiazolin-3-one (OIT). They are available from the Rohm and Haas Company, Philadelphia, Pa. The preferred biocide is DCOIT.

The preferred range of biocide in the composition of the present invention is 1 percent to 15 percent by weight, more preferably 8 to 12% by weight; most preferably 10 percent by weight.

Optional ingredients include, but are not limited to lubricants, process aids, light stabilizers, antioxidants, heat stabilizers, slip agents, anti-block agents, anti-static agents and pigments.

The practice of the present invention is described herein:

EVALUATION OF POLYMER AND BIOCIDE COMPATIBILITY

Blank films of each polymer were prepared by fusing 100 grams of polymer material on a two-roll mill and then molding them with a heated press. The mill temperature was adjusted to allow the polymer to be processed. The warm films were trimmed and about 50 grams of material was placed in a 6 inch by 6 inch by 0.075-inch mold and pressed in a heated press. The mold was then cooled and the films removed. The following polymers were prepared.

Elvaloy® 471 P (Ethylene—Vinyl Acetate—Carbon Monoxide)
Kraton® DRP 6433 (Styrene—Butadiene—Styrene)
Dylark® 332-80 (Styrene—Maleic Anhydride)
NAS 21 (Styrene—Methyl Methacrylate)
NAS 30 (Styrene—Methyl Methacrylate)
Morthane® PS-62 (Thermoplastic polyurethane)
Elvax® 260 (Ethylene—Vinyl acetate)
Pacrel® K (Acrylic Rubber)
Eastman SP 2260 (Ethylene—Methyl Acrylate)
Optema® TC-220 (Ethylene—Methyl Acrylate)
LC 195-136 B (Filled SEBS compound)
LC 195-136C (Unfilled SEBS compound)
Kraton® FG-1901X (SEBS—Maleic Anhydride).

The test films were prepared by fusing 90 grams of polymer on a two-roll mill. When the polymer was fully banded on the mill, 10 grams of the DCOIT (4,5-dichloro-2-n-octyl-4-isothiazolin-3-one) was added at the nip of the rolls. The DCOIT was fully mixed into the fused polymer to form the resin immobilized biocide film. The films were molded in the same way as the blank films.

The resin immobilized biocide films were wrapped in aluminum foil and stored at room temperature. The compatibility of the DCOIT in each polymer was evaluated by visual observation and by the feel of the surface compared to the blank.

After two months at room temperature the following films showed signs of bloom indicating lack of compatibility with the biocide.

Eastman SP 2260 (Ethylene—Methyl Acrylate)
Optema® TC-220 (Ethylene—Methyl Acrylate)
LC 195-136 B (Filled SEBS compound)
LC 195-136C (Unfilled SEBS compound)
Kraton® FG-1901X (SEBS—Maleic Anhydride).

mixed with 112.5 grams of low-density polyethylene (LDPE) plastic and fused on a two-roll mill to form a film. The films were molded in the same way as the blank film.

The samples were evaluated for resistance to microorganisms.

TABLE 1

|  | Low Density Polyethylene Blank | Low Density Polyethylene (LDPE) With 1000 ppm Resin Immobilized Biocide (DCOIT) |
|---|---|---|
| *Staphylococcus aureus* | | |
| Zone of inhibition (mm) | 0 | 15 |
| Growth in the Contact Area | Growth in Contact Area | No Growth in Contact Area |
| *Klebsiella pneumoniae* | | |
| Zone of inhibition (mm) | 0 | 8 |
| Growth in the Contact Area | Growth in Contact Area | No Growth in Contact Area |
| Pink Stain Test | | |
| Zone of inhibition (mm) | 0 | 7 |
| Stain | Light Stain | No Stain |
| ASTM G-24-96 | | |
| Fungal Growth | Light Growth | No Growth |
| *Aspergillus niger* | | |
| AATCC Test Method 30–89 | | |
| Zone of inhibition (mm) | 0 | 15 |
| Growth | Trace to Light Growth | No Growth |

PREPARATION OF THE RESIN IMMOBILIZED BIOCIDE CONCENTRATE BY EXTRUSION

A resin immobilized biocide blend was prepared by mixing 895 grams of Ethylene—Vinyl Acetate-Carbon Monoxide resin with 105 grams of 4,5-dichloro-2-n-octyl-4-isothiazolin-3-one (DCOIT) in a low intensity mixer.

A 0.75-inch single screw extruder, equipped with a single 0.125-inch diameter strand die, was heated to 125° C. to 150° C. The screw speed was set at 50 rpm.

The blend was fed into the extruder. The resulting strand was water-cooled and pelletized.

PREPARATION OF RESIN IMMOBILIZED BIOCIDE CONCENTRATE AND USE OF SAID RESIN IMMOBILIZED BIOCIDE CONCENTRATE IN LOW DENSITY POLYETHYLENE (LDPE) PLASTIC

A film of low-density polyethylene plastic was prepared by fusing 120 grams of material on a two-roll mill. The warm film was trimmed and about 50 grams of material was placed in a 6 inch by 6 inch by 0.075-inch mold. The mold was pressed in a heated press. The mold was then cooled and the films removed.

A blend of 10% DCOIT in 90% Ethylene—Vinyl Acetate (EVA) resin immobilized biocide was prepared on a two-roll mill. 12.5 grams of said resin immobilized biocide was

PREPARATION OF RESIN IMMOBILIZED BIOCIDE CONCENTRATE AND USE OF SAID RESIN IMMOBILIZED BIOCIDE CONCENTRATE IN A WOOD-PLASTIC COMPOSITION

A blend was prepared by mixing 895 grams of Ethylene—Vinyl Acetate-Carbon Monoxide resin with 105 grams of 4,5-dichloro-2-n-octyl-4-isothiazolin-3-one (DCOIT) in a low intensity mixer. The material was melt mixed and formed using a 0.75-inch single screw extruder, equipped with a single 0.125-inch diameter strand die. The extruder was heated from 80° C. to 140° C. The screw speed was set at 70 rpm. The resulting strand was water-cooled and pelletized.

A high density polyethylene plastic that contained from 40% to 60% wood flower and other additives was obtained from a wood-plastic compounder. A film was prepared by fusing 99 g of the wood-plastic compound on a two-roll mill set at 340° F. 1 gram of the resin immobilized biocide concentrate prepared above was added to the wood plastic compound. This material was mixed on the mill for four minutes before being sheeted off. A blank sample was prepared by fusing 100 grams of the wood-plastic compound on the two-roll mill and processed for four minutes before being sheeted off. The samples were evaluated for resistance to microorganisms.

TABLE 2

|  | Wood-plastic compound Blank | Wood-plastic compound With 1000 ppm Resin Immobilized Biocide (DCOIT) |
|---|---|---|
| ASTM G-21-96 | | |
| Fungal Growth | Heavy Growth | No Growth |
| Pink Stain Test | | |
| *Stv. Reticulum* | | |
| Zone of inhibition (mm) | 0 | 7 |
| Stain | Heavy Stain | No Stain |
| *Aspergillus niger* | | |
| AATCC Test Method 30–89 | | |
| Zone of inhibition (mm) | 0 | 0 to 10+ |
| Growth | Heavy Growth | No Growth |

Tables 1 and 2 show that the resin immobilized biocide of the present invention is effective in controlling microorganisms.

What is claimed is:

1. A composition comprising:

(a) 85% to 99% by weight of a resin selected from the group consisting of Ethylene-Vinyl Acetate-Carbon Monoxide; Styrene-Butadiene-Styrene; Styrene-Maleic Anhydride; Styrene-Methyl Methacrylate; Thermoplastic polyurethane; Ethylene-Vinyl Acetate; and Acrylic Rubber; and mixtures thereof:

(b) 1% to 15% by weight of a biocide consisting essentially of 4,5,-dichloro-2-n-octyl4-isothiazolin-3-one biocide (DCOIT) or 2-n-octyl-4-isothiazolin-3-one (OIT).

2. A composition according to claim 1, wherein the resin is Ethylene-Vinyl Acetate-Carbon Monoxide and the biocide is 4,5 dichloro-2-n-octyl-4-isothiazolin-3-one.

3. A composition according to claim 2, wherein the percent by weight of biocide is 10%.

4. A method of inhibiting the growth of bacteria, mold and fungi in a plastic article comprising adding to said plastic article a composition according to claim 1.

* * * * *